US011097124B2

United States Patent
Kim et al.

(10) Patent No.: US 11,097,124 B2
(45) Date of Patent: Aug. 24, 2021

(54) LIGHT TREATMENT APPARATUS AND METHOD OF CONTROLLING THE SAME

(71) Applicant: LUTRONIC CORPORATION, Goyang (KR)

(72) Inventors: Won Joong Kim, Goyang (KR); Jong Tae Kim, Seoul (KR)

(73) Assignee: LUTRONIC CORPORATION, Goyang (KR)

( * ) Notice: Subject to any disclaimer, the term of this patent is extended or adjusted under 35 U.S.C. 154(b) by 174 days.

(21) Appl. No.: 16/226,347

(22) Filed: Dec. 19, 2018

(65) Prior Publication Data

US 2019/0184192 A1 Jun. 20, 2019

(30) Foreign Application Priority Data

Dec. 19, 2017 (KR) .................. 10-2017-0174969

(51) Int. Cl.
| | |
|---|---|
| A61N 5/06 | (2006.01) |
| A61B 18/20 | (2006.01) |
| A61B 18/00 | (2006.01) |
| A61N 5/00 | (2006.01) |
| A61B 17/00 | (2006.01) |
| A61N 5/067 | (2006.01) |

(52) U.S. Cl.
CPC ............ *A61N 5/0616* (2013.01); *A61B 18/20* (2013.01); *A61N 5/062* (2013.01); *A61B 18/203* (2013.01); *A61B 2017/00057* (2013.01); *A61B 2018/00452* (2013.01); *A61B 2018/2035* (2013.01); *A61N 2005/007* (2013.01); *A61N 2005/067* (2013.01); *A61N 2005/0626* (2013.01); *A61N 2005/0643* (2013.01); *A61N 2005/0644* (2013.01); *A61N 2005/0659* (2013.01)

(58) Field of Classification Search
CPC .................. A61B 18/20; A61B 18/203; A61B 2018/00452; A61B 2018/20351; A61B 2018/20355; A61B 2018/2255
See application file for complete search history.

(56) References Cited

U.S. PATENT DOCUMENTS

| | | |
|---|---|---|
| 2005/0154380 A1 | 7/2005 | DeBenedictis et al. |
| 2011/0073778 A1 | 3/2011 | Natori et al. |

(Continued)

FOREIGN PATENT DOCUMENTS

| | | | |
|---|---|---|---|
| JP | 2003319947 A | | 11/2003 |
| JP | 200401995 | * | 7/2004 |
| JP | 2004201995 A | | 7/2004 |

(Continued)

*Primary Examiner* — Allen Porter (57) ABSTRACT

The present invention relates to a light treatment apparatus and a method of controlling the same, and provides to a light treatment apparatus and a method of controlling the same, including: a treatment light irradiating unit for irradiating a treatment region with treatment light a plurality of times while moving on the treatment region; a sensing unit for detecting movement information of the treatment light irradiating unit; and a control unit for controlling an irradiation pattern of the treatment light based on the detected movement information such that an irradiation area of the treatment light to be irradiated from the treatment light irradiating unit overlaps at least in part with an irradiation area of the treatment light which is previously irradiated.

16 Claims, 11 Drawing Sheets

(56) References Cited

U.S. PATENT DOCUMENTS

2012/0283712 A1* 11/2012 Youngquist .......... A61B 18/203
606/9
2013/0268031 A1 10/2013 Ko

FOREIGN PATENT DOCUMENTS

| JP | 2007531558 A | 11/2007 |
| JP | 2011072537 A | 4/2011 |
| KR | 20110015986 A | 2/2011 |
| KR | 101269970 B1 | 5/2013 |
| WO | 2005063138 A1 | 7/2005 |

* cited by examiner

LIGHT TREATMENT APPARATUS AND METHOD OF CONTROLLING THE SAME

CROSS-REFERENCE TO RELATED APPLICATIONS

Priority to Korean patent application number 10-2017-0174969 filed on Dec. 19, 2017, the entire disclosure of which is incorporated by reference herein, is claimed.

BACKGROUND OF THE INVENTION

Field of the Invention

The present invention relates to a light treatment apparatus and a method of controlling the same, and more particularly, to a light treatment apparatus and a method of controlling the same, irradiating a plurality of positions with treatment light while moving on a treatment region.

Discussion of the Related Art

Recently, a technology for treating human body tissue in such a way that treatment energy is transferred to the human body tissue in order to change the state of the human body tissue or remove the human body tissue has been widely applied. Accordingly, treatment apparatuses using various types of electromagnetic waves such as a laser beam, a flash lamp, an RF wave (radio frequency wave), a microwave, an ultrasound, etc. have been developed.

Particularly, an apparatus for irradiating light as treatment energy has been widely used as a treatment apparatus for treatment of skin lesions, and this apparatus is also disclosed in KR Patent Registration No. 10-1269970. When light with a specific wavelength is irradiated onto the skin tissue, the light penetrates into the skin, and according to the wavelength characteristics, is absorbed into various tissues such as collagen, hair follicles, and hemoglobin, which are located under the skin. Then, the absorbed light is converted into thermal energy in the tissues to cause thermal damage to the corresponding tissues, thereby carrying out treatment while changing the state of the tissues.

Such a light treatment apparatus generally includes a handpiece, so a user may proceed treatment by irradiating a treatment region with treatment light a plurality of times while moving the handpiece on the treatment region. The amount of energy delivered to the treatment region varies depending on the irradiation distribution of the treatment light, by which treatment effect is determined.

The conventional light treatment apparatus irradiates treatment light at a predetermined period or by the user's firing operation while the handpiece is moving. Therefore, when the moving speed of the handpiece is not constant, it is difficult to perform uniform treatment, and there is a problem that the treatment effect differs depending on the skill of the user.

SUMMARY OF THE INVENTION

The present invention is to provide a light treatment apparatus and a method of controlling the same capable of transferring an appropriate amount of treatment energy to a treatment position without being greatly affected by the moving speed of the handpiece or the skill of the user.

In order to achieve the object of the present invention described above, the present invention provides a light treatment apparatus including: a treatment light irradiating unit for irradiating a treatment region with treatment light a plurality of times while moving on the treatment region; a sensing unit for detecting movement information of the treatment light irradiating unit; and a control unit for controlling an irradiation pattern of the treatment light based on the detected movement information such that an irradiation area of the treatment light to be irradiated from the treatment light irradiating unit overlaps at least in part with an irradiation area of the treatment light which is previously irradiated.

The control unit may adjust an irradiation time of the treatment light based on the movement information detected by the sensing unit.

Specifically, the control unit may control the treatment light to be sequentially irradiated a plurality of times, and controls the next treatment light to be irradiated when detecting that the treatment light irradiating unit has moved a predetermined distance after irradiation of the previous treatment light.

Alternatively, the control unit may control an irradiation time of the treatment light to be faster than a reference period if a moving speed of the treatment light irradiating unit is faster than a predetermined reference moving speed, and control the irradiation time of the treatment light to be later than the reference period if the moving speed of the treatment light irradiating unit is slower than the predetermined reference moving speed Here, the control unit may control the irradiation pattern of the treatment light such that the irradiation areas of two treatment lights which are adjacently irradiated onto the treatment region overlap with each other at a predetermined ratio.

The irradiation area may be formed in a circular spot shape having a predetermined diameter on the treatment region, and the predetermined overlapping ratio may be 10% to 25% based on the diameter of the irradiation area.

Further, the light treatment apparatus may include a setting unit for setting a ratio at which the irradiation areas of two treatment lights, which are adjacently irradiated onto the treatment region, overlap with each other. The setting unit may provide a plurality of overlapping ratio options so that a user can select the overlapping ratio. In addition, the control unit may control the irradiation pattern of the treatment light such that the treatment lights which are adjacently irradiated overlap with each other at the overlapping ratio the user have selected.

The object of the present invention described above may be achieved by a method of controlling a light treatment apparatus including the steps of: irradiating a treatment region with a first treatment light by operating a treatment light irradiating unit; detecting a distance that a handpiece moves from a position irradiated with the first treatment light; and irradiating a second treatment light based on the detected movement distance such that the second treatment light overlaps at least in part with an area irradiated with the first treatment light.

Here, the step of irradiating the second treatment light may be irradiating the second treatment light such that the irradiation area of the second treatment light overlaps with the irradiation area of the first treatment light at a predetermined ratio Specifically, the second treatment light irradiating step may be irradiating the second treatment light when it is detected that the handpiece has moved by a predetermined distance.

The first treatment light and the second treatment light may be irradiated onto the treatment region in the form of a circular spot having a predetermined diameter, wherein in the step of irradiating the second treatment light, a ratio at which the irradiation area of the second treatment light and the irradiation area of the first treatment light overlap with each other may be by a distance of 10% to 25% of the diameter.

Further, this method of controlling the light treatment apparatus may further include: setting a ratio at which the irradiation area of the first treatment light and the irradiation area of the second treatment light overlap with each other. In addition, the second treatment light irradiating step may be irradiating the irradiation area of the second treatment light to overlap with the irradiation area of the first treatment light based on the overlapping ratio set in the setting step. Further, the object of the present invention described above may be achieved by a treatment method using a light treatment apparatus including the steps of: irradiating a treatment region with a first treatment light by using a handpiece; moving the handpiece on the treatment region; and irradiating the treatment region with a second treatment light by detecting movement information of the handpiece such that the second treatment light overlaps at least in part with an area irradiated with the first treatment light.

DETAILED DESCRIPTION OF THE EMBODIMENTS

Hereinafter, a light treatment apparatus according to an embodiment of the present invention will be described in detail with reference to the drawings. In the following description, the positional relationship of each component is principally described based on the drawings. The structure of the invention in the drawings may be illustrated, for the convenience of description, as simplified or exaggerated if necessary. Therefore, the present invention is not limited thereto, and other than these, various devices may be, of course, added, changed, or omitted.

Hereinafter, the term "light treatment apparatus" includes all light treatment apparatuses for treating mammals including humans. That is, the light treatment apparatus includes various light treatment apparatuses used for the purpose of improving the state of a lesion or tissue. In the present embodiment, a structure using a laser as a treatment light is mainly described, but the present invention is not limited thereto, and various kinds of light sources can be used.

Hereinafter, the term "treatment region" refers to a tissue that requires treatment among various kinds of mammalian body organs including human body organs. In the following, a light treatment apparatus for a skin tissue as a treatment region will be mainly described, but the present invention is not limited thereto.

Hereinafter, a light treatment apparatus according to an embodiment of the present invention will be described with reference to FIGS. 1 and 2.

Figure 1:
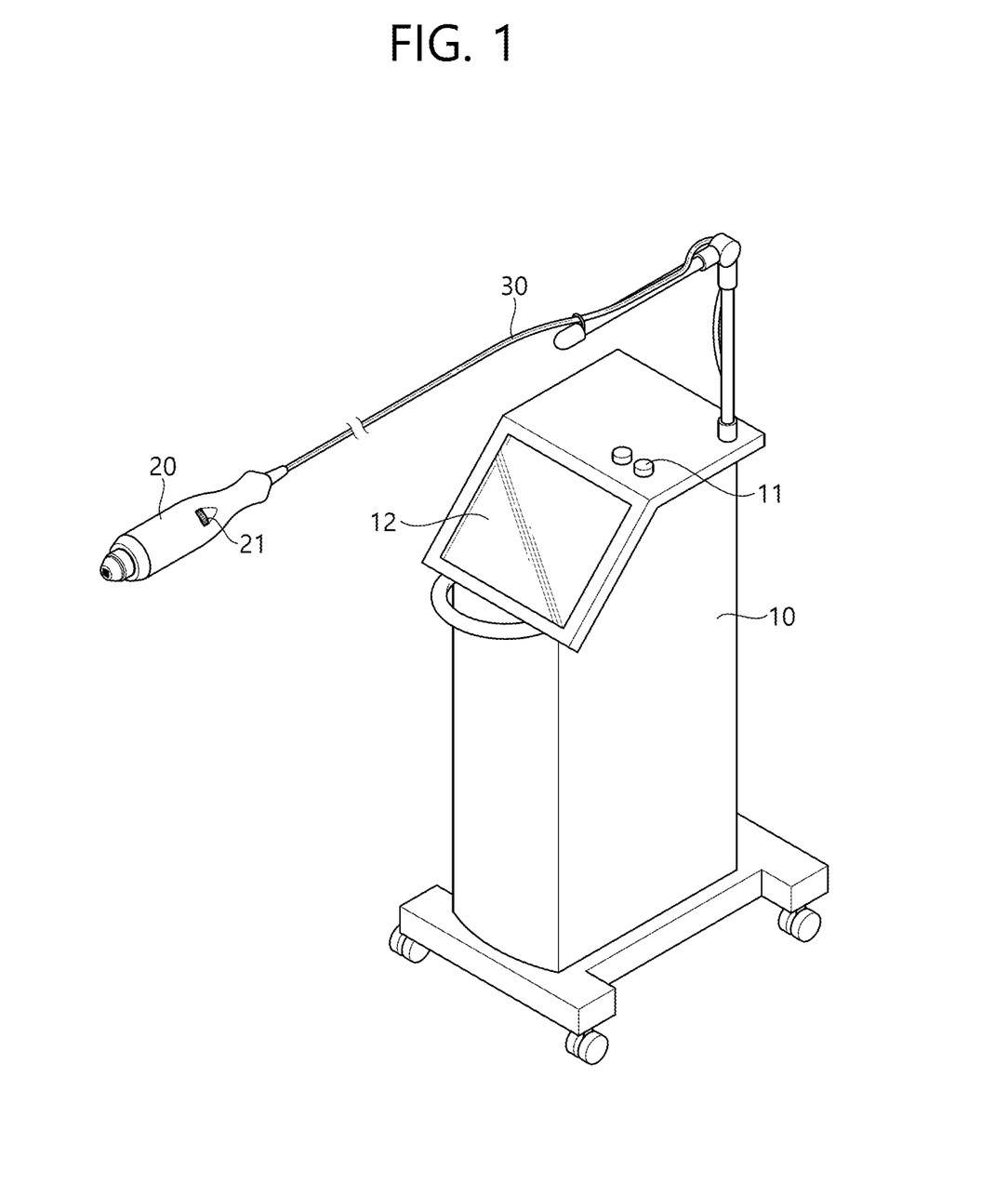
FIG. 1 is a perspective view illustrating a light treatment apparatus according to an embodiment of the present invention.

FIG. 1 is a perspective view illustrating a light treatment apparatus according to an embodiment of the present invention. As shown in FIG. 1, the light treatment apparatus according to the present embodiment includes a main body 10, a handpiece 20, and a connection unit 30 connecting the main body 10 and the handpiece 20.

The main body 10 forms a main frame of the light treatment apparatus, and various components are installed therein. In the main body 10, a treatment light generating unit 110 for generating treatment light and various optical elements for transmitting the treatment light may be provided. On the outer surface of the main body 10, a control panel 11 for operating the treatment apparatus or for setting operation contents, and a display 12 for displaying various information to a user may be installed.

The handpiece 20 is configured in a shape that can be gripped by the user. The user may change a treatment position while holding the handpiece 20 in his hand and may proceed with the treatment. The handpiece 20 includes a treatment light irradiating unit 210 for irradiating treatment light generated in the treatment light generating unit 110 to a treatment region. On the outer surface of the handpiece 20, an operation unit 220 for controlling the operation of the handpiece is provided. Sensors (not shown) or the like for detecting various information during the treatment may be installed in the handpiece.

The connection unit 30 is configured to connect the main body 10 and the handpiece 20 described above. In the connection unit 30, a light transmitting part 310 for forming a light path from the treatment light generating unit 110 of the main body 10 to the treatment light irradiating unit 210 of the handpiece 20 is provided, and a signal line 320 for transmitting various control signals generated from a control unit 120 of the handpiece 20 or the operation unit 220 of the handpiece 20.

Figure 2:
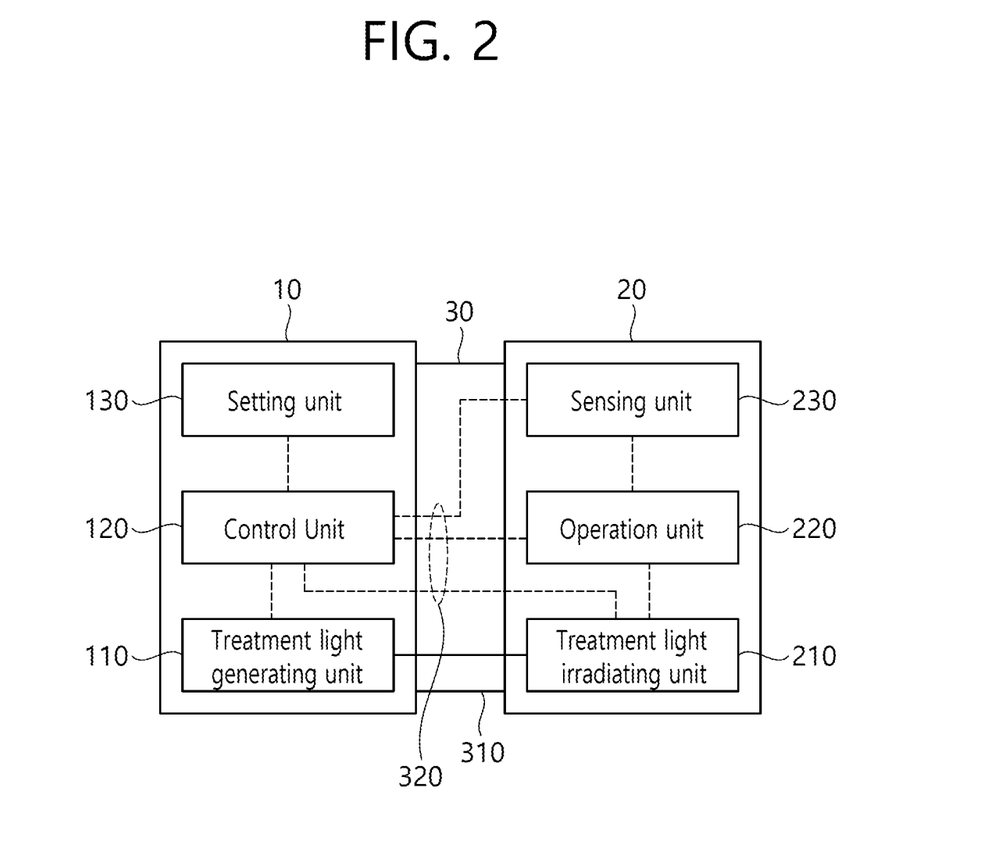
FIG. 2 is a block diagram illustrating the main configuration of FIG. 1.

FIG. 2 is a block diagram schematically illustrating the main configuration of FIG. 1 Hereinafter, with reference to FIG. 2, each configuration shown in FIG. 1 will be described in more detail.

As shown in FIG. 2, the treatment light generating unit 110 is provided in the main body 10. The treatment light generating unit 110 is configured to generate the treatment light as described above. The treatment light generating unit 110 may use various kinds of light source depending on the characteristics of the light treatment apparatus. In the present embodiment, the treatment light generating unit 110 is configured to include a laser medium capable of oscillating a laser and a resonator. However, various light sources such as a light-emitting diode (LED), a laser diode(LD), and a flash lamp can be used according to the purpose of the treatment apparatus other than the above configuration.

More specifically, the treatment light generating unit 110 of the present embodiment can use Neodymium:Yttrium-Aluminum-Garnet (Nd:YAG) or Alexandrite as a laser medium. Therefore, the treatment light generated in the treatment light generating unit 110 may be a laser having a wavelength (Nd:YAG) in the range of 1060 nm to 1070 nm or a laser having a wavelength(Alexandrite) in the range of 750 nm to 760 nm, more specifically, a laser having a wavelength of about 1064 nm or a laser having a wavelength of about 755 nm. However, the light treatment apparatus according to the present embodiment is intended to treat rejuvenation or pigment lesions of the skin and selects a wavelength that is effective for the treatment, and it is also possible to use a laser medium that generates other than the above wavelengths On one side of the treatment light generating unit 110, various optical elements for processing and transmitting treatment light are disposed. The treatment light having passed through the optical elements is transmitted to the treatment light irradiating unit 210 of the handpiece 20 through the light transmitting part 310 of the connection unit 30. Here, the light transmitting part 310 may be composed of at least one optical fiber, or may have a light transmitting structure including a plurality of relay lenses or the like. The treatment light irradiating unit 210 includes various optical elements including a lens, and focuses the treatment light transmitted from the light transmitting unit 310 or processes it to a predetermined spot size to irradiate the treatment region.

However, in the present embodiment, the treatment light generating unit 110 is provided in the main body 10, but this is an example, and it is possible that the treatment light generating unit may be provided in the handpiece itself. In this case, the light transmission part of the connection unit may be omitted, and the treatment light irradiating unit of the handpiece itself may be configured to include a light source and optical elements.

On the other hand, the control unit 120 is configured to control each component of the light treatment apparatus. The control unit 120 controls the operation contents of the light treatment apparatus according to contents set by the user through the control panel 11, contents operated by the user through the operation unit 220 of the handpiece 20, or contents stored in its own memory or the like.

As an example, the control unit 120 controls the treatment light generating unit 110 and the optical elements disposed on the optical path to control the irradiation pattern or parameter of the treatment light. Specifically, it adjusts the irradiation time of the treatment light, the duration and output of the treatment light, and the like by controlling the operation of a flash lamp or a shutter that excites the laser. Alternatively, it can control the spot size and the like of the treatment light by controlling a movable lens or the like which forms the optical path.

Further, in addition to the treatment light, the control unit 120 may variously control the contents of the display, the operation of a cooling unit in the case the cooling unit is provided, or treatment contents based on the information detected by a sensing unit described later.

Figure 3:
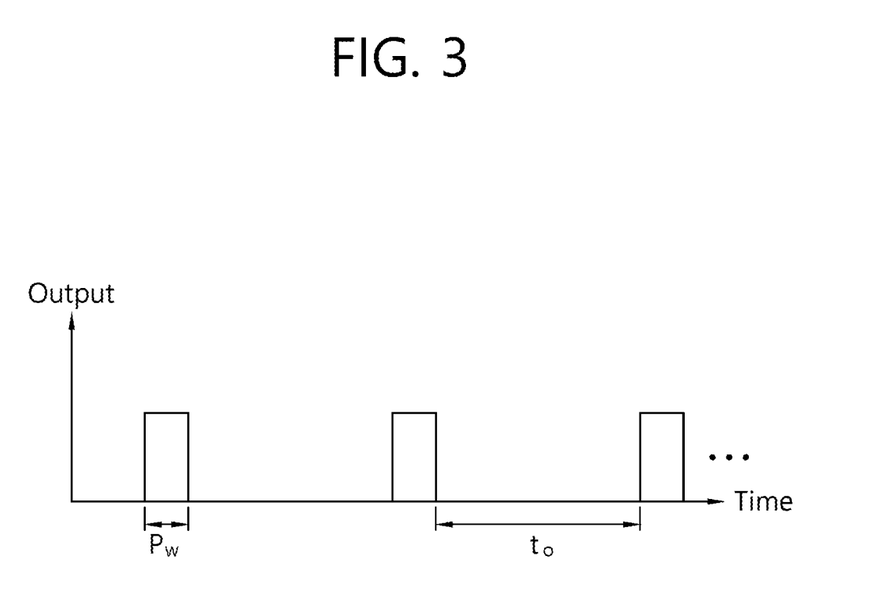
FIG. 3 is a view illustrating an example of an irradiation pattern of treatment light during treatment.

FIG. 3 is a view illustrating an example of an irradiation pattern of treatment light during treatment. The treatment light irradiated through the handpiece 20 may be composed of optical pulses having a predetermined pulse width Pw. However, such optical pulses may be composed of a single pulse or a set of a plurality of unit pulses. As shown in FIG. 3, the treatment light is irradiated a plurality of times while the treatment is proceeding. A plurality of treatment lights are sequentially irradiated at time intervals, and there is an off-time (to) between the irradiation times of the respective treatment lights.

Generally, the treatment using such a light treatment apparatus is operated in such a manner that the user irradiates a treatment region with a plurality of treatment lights while moving the handpiece onto the treatment region. Thus, since the treatment is performed while the handpiece is moved, if the treatment light is irradiated at the same time period, the distribution of the treatment light irradiated onto the treatment region may be different according to the moving speed of the handpiece. In this case, when the user quickly moves the handpiece, the plurality of treatment lights are irradiated at a wide interval, and when the handpiece is slowly moved, they are irradiated at a narrow interval. Therefore, the intensity of treatment differs depending on the user, and even with the same user, different treatment intensity may occur depending on the position.

Therefore, the present embodiment further includes a sensing unit 230 for detecting movement information of the handpiece, and is configured to control the irradiation pattern of the treatment light based on the movement information detected by the sensing unit 230. Therefore, it is possible to treat the treatment region evenly without being affected by the moving speed of the handpiece.

Referring again to FIG. 2, the sensing unit 230 is provided in the handpiece, and is configured to detect the movement information of the handpiece in real time. The sensing unit 230 may be constituted by using sensors such as a distance sensor, a speed sensor, and a gyro sensor. The movement information of the handpiece detected by the sensing unit 230 is transmitted to the control unit 120, and the control unit 120 controls the irradiation pattern of the treatment light based on the movement information.

As an example, the sensing unit 230 may be configured to detect a movement distance of the handpiece. Therefore, the sensing unit 230 can measure the movement distance of the handpiece from the time when the treatment light is irradiated or the time when the treatment light irradiation is completed, and determine the irradiation point of the next treatment light based on the moved distance. In the case of depending on this operation, the plurality of treatment lights sequentially irradiated can be controlled so as to be irradiated, after moving a predetermined interval, from the irradiation area of the treatment light which are previously irradiated.

As another example, it is possible to configure the sensing unit 230 to detect the moving speed of the handpiece. For example, the light treatment apparatus controls the treatment light to be irradiated at a predetermined period in a range in which the handpiece moves at a predetermined reference moving speed, and when the moving speed of the handpiece deviates from the reference moving speed, it is possible to adjust the treatment light irradiation period in consideration of the moving speed of the handpiece If the moving speed of the handpiece detected is faster than the predetermined reference moving speed, the control unit 120 can adjust the irradiation time of the next treatment light to be faster than the reference period. On the other hand, if the moving speed is slower than the predetermined reference moving speed, the control unit 120 may adjust the irradiation time of the next treatment light to be later than the reference period.

In addition, the sensing unit 230 may be configured to detect the moving direction of the handpiece, so that when the moving direction of the handpiece is reversely changed, it is possible that the control unit 120 controls the irradiation of the treatment light to be stopped in order to prevent irradiation of the treatment light again to the irradiated treatment region.

In this way, the sensing unit 230 can select and adopt one of various sensors that measure information necessary to determine distance information such as distance, speed, and acceleration and the like. In addition, the contents that the control unit 120 controls the irradiation pattern of the treatment light based on the detected information may be described in various viewpoints such as an irradiation period of treatment light, an off-time between treatment lights, and an irradiation point of treatment light and the like, As such, it is noted that the technique of controlling the plurality of treatment lights to be irradiated at uniform intervals based on the movement information of the handpiece detected by the sensing unit can be modified and implemented in various ways.

Figure 4:
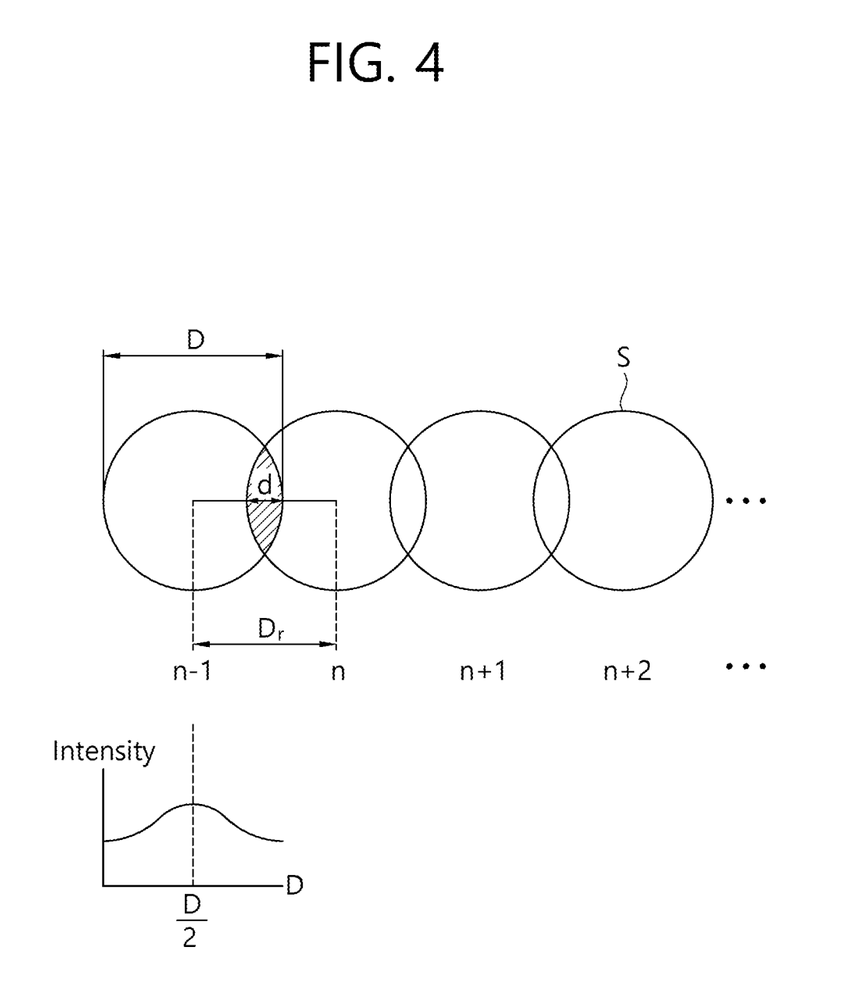
FIG. 4 is a view illustrating a form in which treatment light irradiated by the light treatment apparatus of FIG. 1 is irradiated in an overlapped manner.

FIG. 4 is a view illustrating a form in which treatment light irradiated by the light treatment apparatus of FIG. 1 is irradiated in an overlapped manner. Here, the irradiation area S of the treatment light is an area irradiated with the corresponding treatment light on the surface of the treatment region and has a meaning that corresponds to a spot of the treatment light that is focused on the surface of the treatment region. The treatment light according to the present embodiment is irradiated in the form of a circular cross section, and has an irradiation area in the form of a spot having a predetermined diameter D.

As shown in FIG. 4, the control unit 120 may control the irradiation of a plurality of treatment lights to be sequentially irradiated in the overlapped manner. That is, when the treatment light is irradiated N times during the treatment, the irradiation area of an $n^{th}$ treatment light may overlap at least in part with the irradiation area of an $(n-1)^{th}$ treatment light which is previously irradiated. In the case the treatment lights are irradiated in the overlapped manner as described above, the portion where the treatment lights are not irradiated onto the treatment region on which the handpiece 20 moves can be minimized.

Further, as shown in FIG. 4, when part of the edges of the treatment lights are irradiated to overlap with each other, there is an advantage of compensating the deviation according to the intensity distribution of the treatment light. That is, although the intensity of the treatment light is relatively large at the central portion on the basis of the cross section of the treatment light and becomes relatively weaker toward the edge, it is possible to compensate the above deviation by having the edges of the irradiation area irradiated in the overlapped manner.

Figure 5:
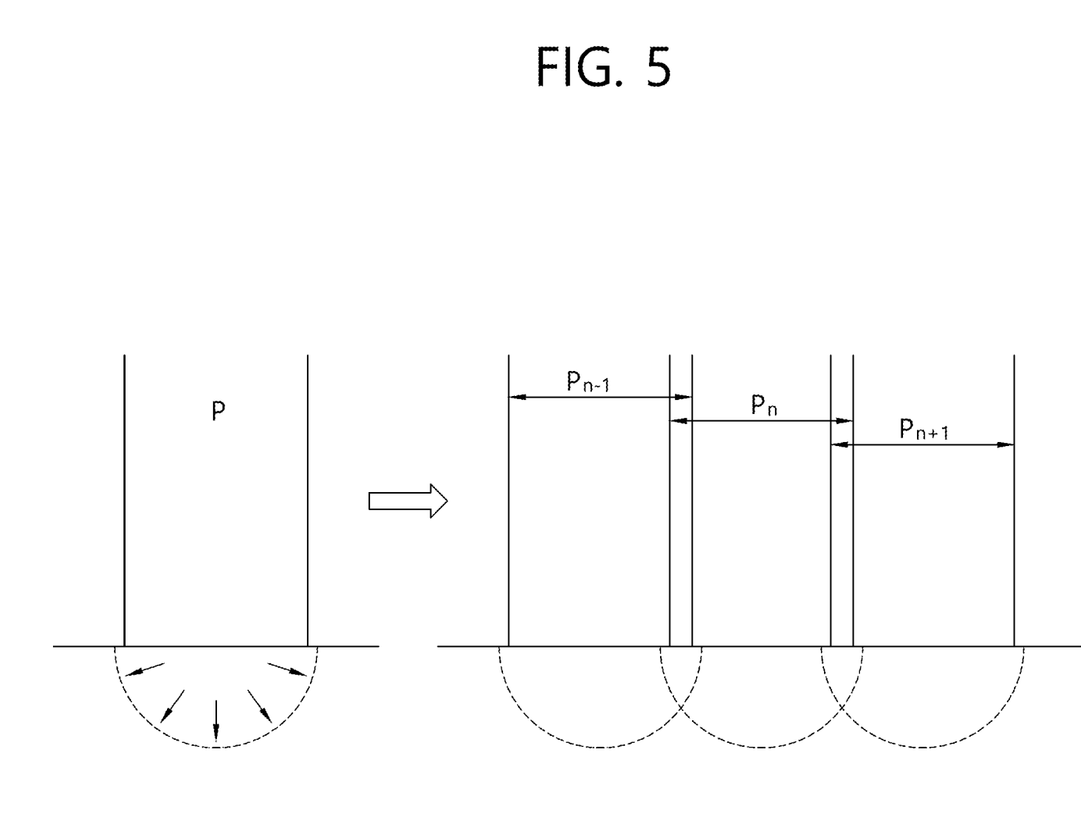
FIG. 5 is a view illustrating thermal distribution in the tissue in the case the treatment light is irradiated in the overlapped manner in FIG. 4.

Further, when the treatment lights are irradiated to overlap each other like this, there is an advantage in that the deviation due to the spatial heat distribution of the tissue that absorbs the energy of the treatment light can be compensated. FIG. 5 is a view illustrating thermal distribution in the tissue in the case the treatment light is irradiated in the overlapped manner in FIG. 4. When the irradiated treatment light is absorbed into the treatment region, the absorbed heat is diffused inside the tissue. As shown in FIG. 5, the heat at the central portion of the treatment light is transferred to a sufficient depth, while the heat at the edge thereof is not transferred to a sufficient depth. This also appears, even when the intensity distribution along the cross section of the treatment light is the same, as a similar type of distribution to this due to heat diffusion characteristic Therefore, as shown in FIG. 4, when the edge is irradiated to be partially overlapped, energy is transferred in an overlapped manner. to the treatment region located at the edge of the treatment light, and heat is transferred to a sufficient depth, so that the spatial thermal distribution deviation of the tissue that absorbs the energy. can be compensated.

The light treatment apparatus according to the present embodiment irradiates the treatment light such that the irradiation areas of the two treatment lights which are adjacently irradiated overlap with each other at the ratio of a predetermined value or range. As described above, since the sensing unit 230 detects movement information of the handpiece in real time, based on this, the control unit 120 can control the overlapping ratio of the irradiation areas of the two treatment lights which are adjacently irradiated in a temporal relation.

Here, the ratio (r) in which the irradiation areas of the two treatment lights overlap with each other can be expressed as the ratio of the length (d) of the overlapping portions on the line connecting the centers of the overlapping irradiation areas with respect to the diameter (D). The overlapping ratio of the two treatment lights may be a ratio that falls within a range of 50% or less. As an example, the overlapping ratio of the present embodiment may be a ratio included in the range of 10% to 25%. More specifically, it may be a ratio included in the range of 15% to 22%.

Figure 6:
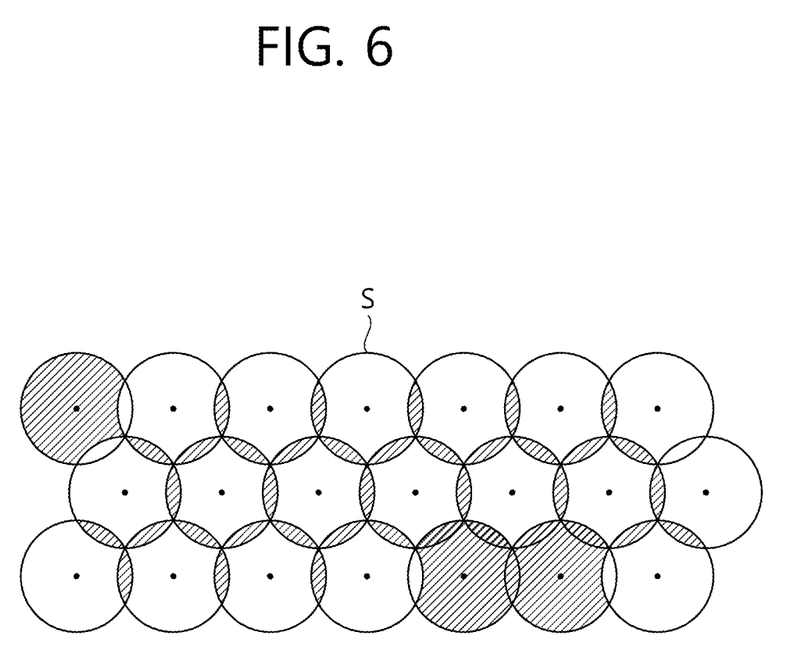
FIG. 6 is a view illustrating an example in which the treatment light irradiated by the light treatment apparatus of FIG. 1 is irradiated onto a treatment region.

FIG. 6 is a view illustrating an example in which the treatment light irradiated by the light treatment apparatus of FIG. 1 is irradiated onto the treatment region. As shown in FIG. 6, according to the present embodiment, the edges of the respective treatment light irradiation areas S are overlapped with each other, so that the area where the treatment light is not irradiated in the direction in which the hand piece advances can be minimized. Further, even in the case of irradiating the treatment region with the treatment light while moving the handpiece in a plurality of rows, as shown in FIG. 6, the treatment light is irradiated to overlap with part of the edges of the row which is previously irradiated, so that it is possible to proceed with the treatment while minimizing the area where the treatment light is not irradiated between the respective rows. In FIG. 6, each the irradiation area arranged in one row shows a pattern irradiated in a form staggered with each of the irradiation area arranged in an adjacent row. However, the present invention is not limited thereto, and various other patterns may be used.

Referring again to FIG. 2, the light treatment apparatus according to the present embodiment further includes a setting unit 130, and the user can select the overlapping ratio of the above-mentioned treatment light through the setting unit 130. The setting unit 130 may include a control panel 11 or a display 12 installed on the outer surface of the above-mentioned main body, and maybe configured as various other structures.

For example, the setting unit 130 may provide various options of the overlapping ratio that the user can select, and may be configured for the user to select the overlapping ratio. For example, the setting unit 130 may provide 0%, 10%, 20%, 30%, and 40% choices through the display 12, and the user can select them. Here, the 0% mode does not mean every state in which the two treatment lights do not overlap with each other, but means that the boundaries of the two treatment lights in the irradiation areas are irradiated at a contact interval. In this case, although the irradiation areas of the two treatment lights do not overlap each other on the surface of the treatment region, an effect of their substantially overlapping with each other inside the tissue can be seen due to heat diffusion. Meanwhile, the overlapping ratio set by the user is transmitted to the control unit, and the irradiation area of the adjacent treatment light can be controlled to overlap at a predetermined overlapping ratio while proceeding with the corresponding treatment.

For example, in controlling the treatment light in such a manner that when the control unit detects that the handpiece has been moved by a reference distance from the time when an $n-1^{th}$ treatment light is irradiated, then the control unit controls the irradiation of an $n^{th}$ treatment light; when the predetermined overlapping ratio is relatively low, the reference distance between points at each of which the treatment light is irradiated can be set to be wider, and when the predetermined overlapping ratio is relatively high, the reference distance between points at each of which the treatment light is irradiated can be set to be narrower. For reference, the reference distance can be derived as follows. (The treatment light moves while the treatment light is irradiated, that is, during the time corresponding to the treatment light pulse width, which can be ignored in the case it is significantly smaller than in comparison with the off-time.)

$Dr=D-D \cdot r$ (Dr: reference distance, D: spot diameter, r: predetermined overlapping ratio)

Figure 7A:
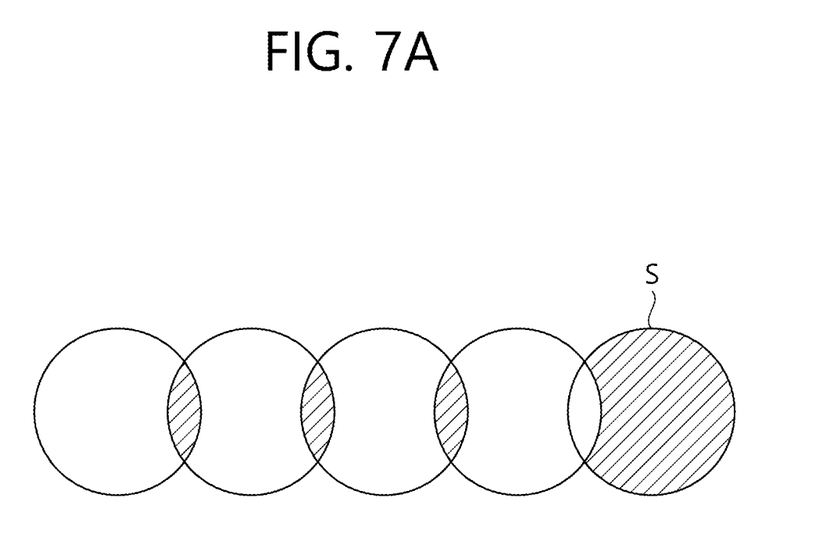
FIGS. 7A and 7B are views illustrating a state of an irradiation areas of the treatment light overlapping at two different overlapping ratios.
Figure 7B:
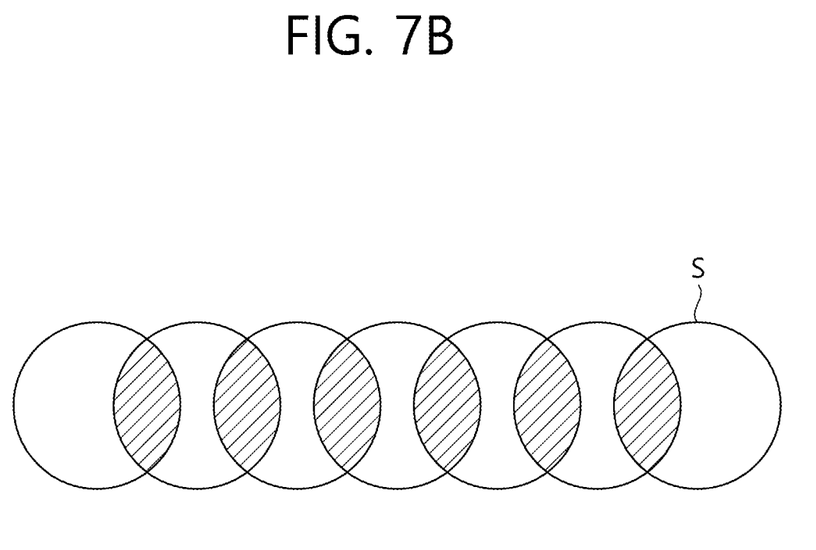

FIGS. 7A and 7B are views illustrating a state of an irradiation areas of the treatment light overlapping at two different overlapping ratios. FIG. 7A shows the state of the treatment light in which the overlapping ratio is 20%, and FIG. 7B shows the state of the treatment light in which the overlapping ratio is 40%. As shown in FIGS. 7A and 7B, when the overlapping ratio is low, the intensity of the treatment light irradiated onto the treatment region is relatively low, and when the overlapping ratio is high, the intensity of the treatment light irradiated onto the treatment region is relatively high. Therefore, according to the present embodiment, by setting the overlapping ratio differently, it is possible to control the treatment intensity of the treatment region even without adjusting the output of the treatment light or the spot size.

Figure 8A:
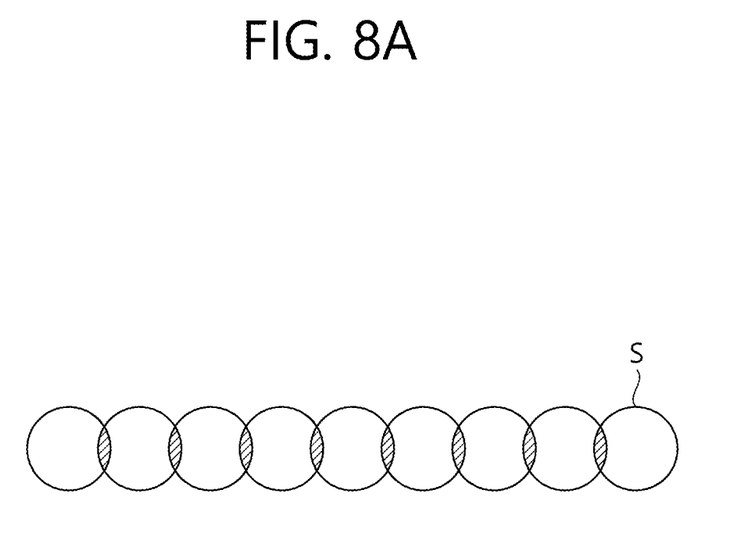
FIGS. 8A and 8B are views illustrating a state in which treatment lights having different spot sizes are irradiated in the overlapped manner.
Figure 8B:
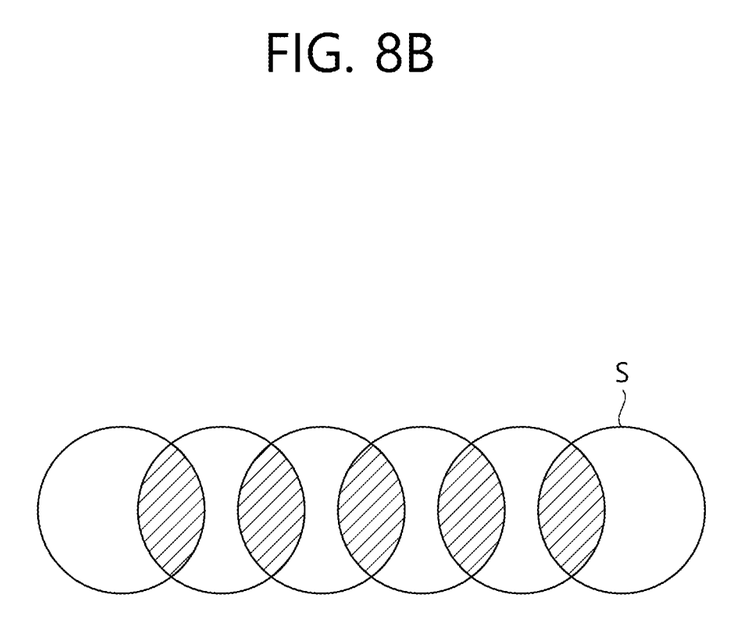

FIGS. 8A and 8B are a views illustrating a state in which treatment lights having different spot sizes are irradiated in the overlapped manner. The setting unit 130 described above can be configured to adjust the spot size of the treatment light. In this case, a narrowly formed treatment region can be easily treated. However, if the spot size of the treatment light generated in the same light source is adjusted, the intensity of the treatment light transmitted per unit area to the treatment region is changed. If the spot size of the treatment light generated from the same light source is adjusted to be small, the intensity of the treatment light to be irradiated onto the irradiation area relatively increases, and if the spot size is adjusted to be large, the intensity of the treatment light is relatively decreased. Therefore, in the present embodiment, the overlapping ratio can be adjusted to compensate for the difference in the intensity of the treatment light according to the change in the spot size.

That is, even when the spot size is changed, the control unit 120 may control the overlapping ratio according to the spot size when the treatment is desired to be performed with the same treatment intensity on the treatment region. For example, when the spot size is adjusted to be small, the control unit can control the overlapping ratio to be reduced as well, and if the spot size is adjusted to be large, the control unit can control the overlapping ratio to be increased as well.

Figure 9:
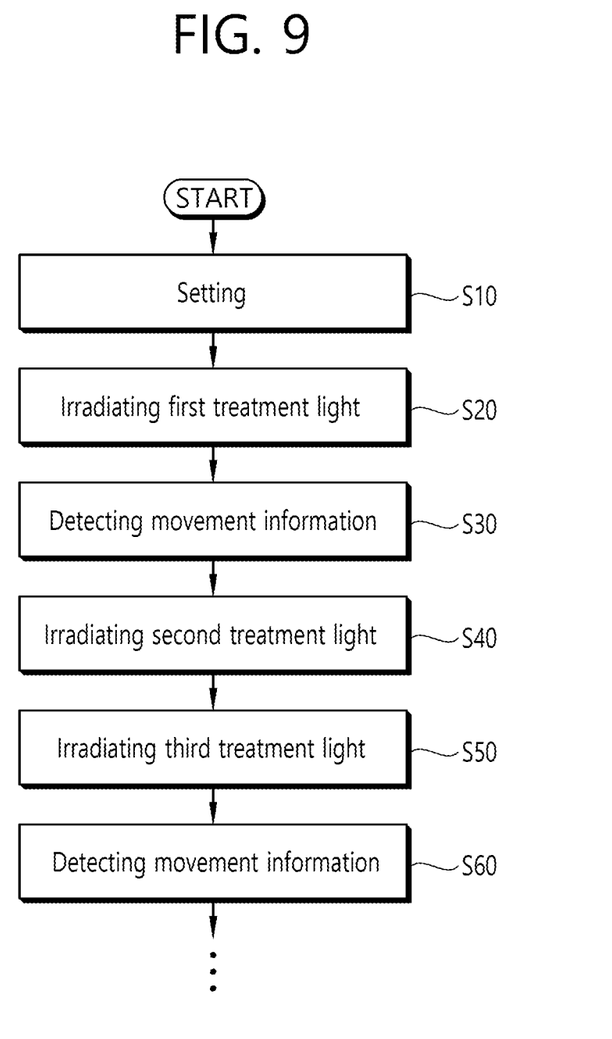
FIG. 9 is a flowchart illustrating a method of controlling the light treatment apparatus of FIG. 1.

FIG. 9 is a flowchart illustrating a method of controlling the light treatment apparatus of FIG. 1; Hereinafter, with reference to FIG. 9, the method of controlling the above-described light treatment apparatus will be described in detail.

First of all, prior to the treatment, the method includes a step of setting treatment contents(S10). In this step, various parameters for the treatment contents as well as a treatment mode can be set. For example, the intensity of treatment light, the spot size, and the overlapping ratio during the treatment light irradiation can be set. Thus, the user sets the appropriate treatment contents in consideration of the treatment region and lesion.

When the above-described setting step is completed, the user can place the handpiece 20 on the skin, which is the treatment region, and then start the treatment. The treatment is performed, for example, by irradiating the treatment light at predetermined intervals while moving the handpiece.

Then, a step of irradiating the treatment region with a first treatment light is performed (S20). In this step, the control unit 120 controls the operation of the treatment light generating unit or the treatment light irradiating unit to generate the treatment light, and the generated treatment light is irradiated onto the treatment region through the end of the handpiece. Here, the first treatment light may be the first treatment light to be irradiated during the treatment, or may be a treatment light selected at an random point in a plurality of treatment lights being irradiated during the treatment. The first treatment light is irradiated so as to have an irradiation area of a circular spot with a diameter of D on the treatment region and is irradiated for a time corresponding to the pulse width of the treatment light and then turned off.

When the first treatment light is irradiated, the sensing unit performs a step of detecting movement information of the handpiece (S30). The movement information of the handpiece is detected by the sensing unit, and the movement information detected by the sensing unit includes a movement distance. The operation of detecting this movement distance in the sensing unit can be continuously performed during the treatment from the beginning of the treatment. However, in FIG. 9, the present step is illustrated as proceeding after the irradiating step of the first treatment light, and this means that the measuring of the movement distance is from the time when the first treatment light is irradiated (or after the time when the irradiation of the first treatment light is finished).

When the first treatment light is irradiated, the control unit 120 detects the movement distance of the handpiece 20 and controls the second treatment light to be irradiated at a predetermined overlapping ratio. Once the overlapping ratio is set in the setting step which is previously performed, a reference distance corresponding to the overlapping ratio is determined. (In the present embodiment, the reference distance is set on the basis of the movement distance during an interval between irradiation starting timing of the two treatment lights to be sequentially irradiated, wherein the interval is the sum of 'Pw' [a pulse width of one treatment light] and 'to' [an off-time between two treatment light], "Pw+to". Alternatively, it is possible that the reference distance is set based on the movement distance during one off-time "to" between two treatment lights. However, if the pulse width is significantly shorter than the off-time, there may be no practical benefit of the above two types of distinction) Accordingly, if the control unit 120 detects through the movement information detecting step that the handpiece moves by the reference distance, then it controls the treatment light generating unit or the treatment light irradiating unit to irradiate a second treatment light (S40). Accordingly, it is possible that the two treatment lights which are adjacently irradiated in a temporal relation can be irradiated to overlap with each other at a predetermined overlapping ratio while irradiating in a state of being spaced apart by the corresponding reference distance.

On the other hand, when the second treatment light is irradiated, then similarly to the step S30, while a step of detecting movement information for measuring a movement distance from the time when the second treatment light is irradiated(S50) is performed, a step of irradiating a third treatment light is performed(S60). Then, these processes can be repeated to irradiate the treatment light up to an $N^{th}$ treatment light.

However, in the flowchart of FIG. 9, although the steps of detecting two pieces of movement information are respectively illustrated as being separative steps, as described above, it is noted that the movement information detecting step may be one step that is continuously performed while the treatment light is irradiated, and may proceed in parallel with each of the treatment light irradiating step at the same time.

As described above, according to the present invention, it is possible to control the irradiation pattern of the treatment light in consideration of the movement information of the handpiece, so that the variation in the treatment intensity according to the characteristics of the user and the treatment position can be minimize and it is possible to proceed with uniform treatment Further, since the treatment lights that are sequentially irradiated are irradiated to overlap each other, it is possible to minimize the treatment region where the treatment light is not irradiated, to compensate for the deviation due to the spatial heat distribution of the tissue that absorbs the energy of the treatment light and the intensity deviation according to the position of the cross section of the treatment light, and to adjust the intensity of the treatment without changing the output of the treatment light through adjusting the overlapping ratio and the spot size.

So far, although one embodiment of the present invention has been described in detail, the present invention is not limited to the above embodiment. It should be noted that the present invention can be implemented as various changes and modifications by a person with ordinary skill in the art without departing from of the scope of the technical feature of the invention as defined in the appended claims.

According to the present invention, since the treatment light is irradiated in consideration of information that the handpiece moves, so that there is an advantage in that uniform treatment is possible.

Also, the treatment lights which are adjacently irradiated are irradiated in a predetermined ratio in an overlapped manner, so that it is possible to minimize the region where the treatment is not performed.

Further, since the overlapping ratio of the treatment lights which are adjacently irradiated can be set, even in the case light having the same parameters is used, it is possible to perform the treatment with various intensities by adjusting the overlapping ratio.

What is claimed is:

1. A light treatment apparatus comprising:
a handpiece including a treatment light irradiating unit for irradiating a treatment region with a plurality of treatment lights, the plurality of treatment lights including first and second treatment lights, the second treatment light being irradiated subsequently to the first treatment light;
a sensing unit for detecting movement information of the handpiece; and
a controller for controlling an irradiation pattern of the plurality of treatment lights based on the detected movement information such that a first irradiation area of the first treatment light overlaps at least in part with a second irradiation area of the second treatment light, wherein the controller controls the irradiation pattern by irradiating the treatment region with the first treatment light and the second treatment light while the handpiece continuously moves over the treatment region such that the first and second irradiation areas overlap with each other at a predetermined overlapping ratio.

2. The light treatment apparatus of claim 1, wherein the controller adjusts an irradiation time of each of the plurality of treatment lights based on the movement information detected by the sensing unit.

3. The light treatment apparatus of claim 1, wherein the controller controls the plurality of treatment lights to be sequentially irradiated, and controls the second treatment light to be irradiated when detecting that the handpiece including the treatment light irradiating unit has moved a reference distance after irradiation of the first treatment light.

4. The light treatment apparatus of claim 3, wherein the reference distance is represented by $Dr=D-D*r$, where Dr denotes the reference distance, D denotes a spot diameter of each of the first and second irradiation areas, and r denotes the predetermined overlapping ratio.

5. The light treatment apparatus of claim 1, wherein the controller controls an irradiation time of each of the plurality of treatment light to be faster than a reference period if a moving speed of the handpiece including the treatment light irradiating unit is faster than a predetermined reference moving speed, and controls the irradiation time to be later than the reference period if the moving speed of the handpiece is slower than the predetermined reference moving speed.

6. The light treatment apparatus of claim 1, wherein each of the first and second irradiation areas is formed in a circular spot shape having a predetermined diameter on the treatment region, and the predetermined overlapping ratio is 10% to 25% based on the predetermined diameter.

7. The light treatment apparatus of claim 1, further comprising: a setting unit for setting the overlapping ratio.

8. The light treatment apparatus of claim 7, wherein the setting unit provides a plurality of overlapping ratio options so that a user can select the overlapping ratio, and
wherein the controller controls the irradiation pattern such that the first and second treatment lights which are adjacently irradiated overlap with each other at the overlapping ratio the user have selected.

9. The light treatment apparatus of claim 1, wherein the controller stops irradiating the treatment region when the sensing unit detects that a moving direction of the handpiece is reversely changed.

10. A light treatment apparatus comprising:
a handpiece including a treatment light irradiating unit for irradiating a treatment region with a plurality of treatment lights, the plurality of treatment lights including first and second treatment lights, the second treatment light being irradiated subsequently to the first treatment light;
a sensing unit for detecting movement information of the handpiece; and
a controller for controlling an irradiation pattern of the plurality of treatment lights based on the detected movement information such that a first irradiation area of the first treatment light overlaps at least in part with a second irradiation area of the second treatment light, wherein the controller controls the irradiation pattern by irradiating the treatment region with the first treatment light and the second treatment light while the handpiece continuously moves over the treatment region such that the first and second irradiation areas overlap with each other at a predetermined overlapping ratio.

11. A method of controlling a light treatment apparatus comprising the steps of:
  irradiating a treatment region with a plurality of treatment lights by operating a treatment light irradiating unit included in a handpiece, the plurality of treatment lights including first and second treatment lights, the second treatment light being irradiated subsequently to the first treatment light;
  detecting movement information of the handpiece; and
  controlling an irradiation pattern of the plurality of treatment lights based on the detected movement information such that a first irradiation area of the first treatment light overlaps at least in part with a second irradiation area of the second treatment light,
  wherein the treatment region is irradiated with the first treatment light and the second treatment light while the handpiece continuously moves over the treatment region such that the first and second irradiation areas overlap with each other at a predetermined overlapping ratio.

12. The method of claim 11, wherein the second treatment light is irradiated when it is detected that the handpiece has moved by a reference distance after irradiation of the first treatment light.

13. The method of claim 11, wherein the first treatment light and the second treatment light are irradiated onto the treatment region in the form of a circular spot having a predetermined diameter,
  wherein the predetermined overlapping ratio is 10% to 25% based on the predetermined diameter.

14. The method of claim 11, further comprising: setting the overlapping ratio,
  wherein the second treatment light is irradiated to make the second irradiation area of the second treatment light overlap with the first irradiation area of the first treatment light based on the overlapping ratio set in the setting step.

15. The method of claim 11, further comprising:
  detecting a distance that the handpiece moves from a position irradiated with the second treatment light; and
  irradiating a third treatment light based on the movement distance after the irradiation of the second treatment light such that a third irradiation area of the third treatment light overlaps at least in part with the second irradiation area of the second treatment light.

16. A treatment method using a light treatment apparatus comprising the steps of:
  irradiating a treatment region with a plurality of treatment lights by using a treatment light irradiating unit included in a handpiece, the plurality of treatment lights including a first treatment light and a second treatment light, the second treatment light being irradiated subsequently to the first treatment light;
  detecting movement information of the handpiece; and
  controlling an irradiation pattern of the plurality of treatment lights based on the detected movement information of the handpiece such that a first irradiation area of the first treatment light overlaps at least in part with a second irradiation area of the second treatment light,
  wherein the treatment region is irradiated with the first treatment light and the second treatment light while the handpiece continuously moves over the treatment region such that the first and second irradiation areas overlap with each other at a predetermined overlapping ratio.

* * * * *